United States Patent
Jafari et al.

(10) Patent No.: US 9,421,338 B2
(45) Date of Patent: *Aug. 23, 2016

(54) VENTILATOR LEAK COMPENSATION

(71) Applicant: Covidien LP, Boulder, CO (US)

(72) Inventors: Mehdi M. Jafari, Laguna Hills, CA (US); Rhomere S. Jimenez, Winchester, CA (US); Edward R. McCoy, Vista, CA (US); Jeffrey K. Aviano, Escondido, CA (US)

(73) Assignee: Covidien LP, Mansfield, MA (US)

( * ) Notice: Subject to any disclaimer, the term of this patent is extended or adjusted under 35 U.S.C. 154(b) by 295 days.

This patent is subject to a terminal disclaimer.

(21) Appl. No.: 13/795,159

(22) Filed: Mar. 12, 2013

(65) Prior Publication Data

US 2013/0186400 A1    Jul. 25, 2013

Related U.S. Application Data

(63) Continuation of application No. 12/414,419, filed on Mar. 30, 2009, now Pat. No. 8,434,480.

(60) Provisional application No. 61/041,070, filed on Mar. 31, 2008.

(51) Int. Cl.
*A61M 16/00* (2006.01)
*A61M 16/06* (2006.01)
(Continued)

(52) U.S. Cl.
CPC ..... *A61M 16/0057* (2013.01); *A61M 16/0051* (2013.01); *A61M 16/04* (2013.01); *A61M 16/06* (2013.01); *A61M 16/0666* (2013.01); *A61M 16/0875* (2013.01); *A61M 2016/0021* (2013.01);
(Continued)

(58) Field of Classification Search
CPC . A61M 16/00; A61M 16/06; A61M 2205/15; A61M 2205/50
See application file for complete search history.

(56) References Cited

U.S. PATENT DOCUMENTS 3,805,780 A    4/1974 Cramer et al.
3,941,124 A    3/1976 Rodewald et al.
(Continued)

FOREIGN PATENT DOCUMENTS

DE    19808543 A1    11/1998
EP    0425092 A    5/1991
(Continued)

OTHER PUBLICATIONS

Younes, M, et al., "Control of breathing relevant to mechanical ventilation", in Physiological Basis of Ventilatory Support, J.J. Marini and A.S. Slutsky, Ed., New York, Marcel Dekker, 1998, pp. 1-73.
(Continued)

*Primary Examiner* — Lynne Anderson
*Assistant Examiner* — Kathryn E Ditmer
(74) *Attorney, Agent, or Firm* — Merchant & Gould P.C.

(57) ABSTRACT

A ventilator including a pneumatic system for providing and receiving breathing gas, and a controller operatively coupled with the pneumatic system. The controller is operable to control circulation by the pneumatic system of breathing gas to and from a patient, and to adjust at least one of a volume and pressure of breathing gas delivered to the patient, such adjustment being based upon elastic properties of a component used to fluidly couple the pneumatic system to a patient.

20 Claims, 3 Drawing Sheets

(51) Int. Cl.
*A61M 16/04* (2006.01)
*A61M 16/08* (2006.01)

(52) U.S. Cl.
CPC ............ *A61M 2016/0027* (2013.01); *A61M 2016/0033* (2013.01); *A61M 2205/15* (2013.01); *A61M 2205/502* (2013.01); *A61M 2205/52* (2013.01); *A61M 2230/46* (2013.01)

(56) References Cited

U.S. PATENT DOCUMENTS

| | | |
|---|---|---|
| 4,056,098 A | 11/1977 | Michel et al. |
| 4,305,388 A | 12/1981 | Brisson |
| 4,340,044 A | 7/1982 | Levy et al. |
| 4,448,192 A | 5/1984 | Stawitcke et al. |
| 4,752,089 A | 6/1988 | Carter |
| 4,766,894 A | 8/1988 | Legrand et al. |
| 4,921,642 A | 5/1990 | LaTorraca |
| 4,939,647 A | 7/1990 | Clough et al. |
| 4,954,799 A | 9/1990 | Kumar |
| 4,971,052 A | 11/1990 | Edwards |
| 4,972,842 A | 11/1990 | Korten et al. |
| 4,986,268 A | 1/1991 | Tehrani |
| 5,057,822 A | 10/1991 | Hoffman |
| 5,065,350 A | 11/1991 | Fedder |
| 5,072,728 A | 12/1991 | Pasternack |
| 5,072,737 A | 12/1991 | Goulding |
| 5,094,235 A | 3/1992 | Westenskow et al. |
| 5,148,802 A | 9/1992 | Sanders et al. |
| 5,150,291 A | 9/1992 | Cummings et al. |
| 5,161,525 A | 11/1992 | Kimm et al. |
| 5,237,987 A | 8/1993 | Anderson et al. |
| 5,239,995 A | 8/1993 | Estes et al. |
| 5,259,373 A | 11/1993 | Gruenke et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,313,937 A | 5/1994 | Zdrojkowski et al. |
| 5,315,989 A | 5/1994 | Tobia |
| 5,316,009 A | 5/1994 | Yamada |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,365,922 A | 11/1994 | Raemer |
| 5,368,019 A | 11/1994 | LaTorraca |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,433,193 A | 7/1995 | Sanders et al. |
| 5,438,980 A | 8/1995 | Phillips |
| 5,443,075 A | 8/1995 | Holscher |
| 5,492,113 A | 2/1996 | Estes et al. |
| 5,503,146 A | 4/1996 | Froehlich et al. |
| 5,503,147 A | 4/1996 | Bertheau |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brody |
| 5,544,674 A | 8/1996 | Kelly |
| 5,549,106 A | 8/1996 | Gruenke et al. |
| 5,551,418 A | 9/1996 | Estes et al. |
| 5,551,419 A | 9/1996 | Froehlich et al. |
| 5,555,880 A | 9/1996 | Winter et al. |
| 5,596,984 A | 1/1997 | O'Mahony et al. |
| 5,598,838 A | 2/1997 | Servidio et al. |
| 5,605,151 A | 2/1997 | Lynn |
| 5,623,923 A | 4/1997 | Bertheau et al. |
| 5,630,411 A | 5/1997 | Holscher |
| 5,632,269 A | 5/1997 | Zdrojkowski |
| 5,632,270 A | 5/1997 | O'Mahony et al. |
| 5,645,048 A | 7/1997 | Brodsky et al. |
| 5,645,053 A | 7/1997 | Remmers et al. |
| 5,650,943 A | 7/1997 | Powell et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,685,296 A * | 11/1997 | Zdrojkowski et al. ..... 128/205.24 |
| 5,687,715 A * | 11/1997 | Landis et al. ............ 128/207.18 |
| 5,692,497 A | 12/1997 | Schnitzer et al. |
| 5,715,812 A | 2/1998 | Deighan et al. |
| 5,719,785 A | 2/1998 | Standifer |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,813,399 A | 9/1998 | Isaza et al. |
| 5,823,187 A | 10/1998 | Estes et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,876,352 A | 3/1999 | Weismann |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,891,023 A | 4/1999 | Lynn |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,927,274 A | 7/1999 | Servidio et al. |
| 5,934,274 A | 8/1999 | Merrick et al. |
| 5,970,975 A | 10/1999 | Estes et al. |
| 6,024,089 A | 2/2000 | Wallace et al. |
| 6,029,664 A | 2/2000 | Zdrojkowski et al. |
| 6,041,780 A | 3/2000 | Richard et al. |
| 6,047,860 A | 4/2000 | Sanders |
| 6,055,981 A | 5/2000 | Laswick et al. |
| 6,059,732 A | 5/2000 | Orr et al. |
| 6,076,523 A | 6/2000 | Jones et al. |
| 6,099,481 A | 8/2000 | Daniels et al. |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,123,074 A | 9/2000 | Hete et al. |
| 6,135,106 A | 10/2000 | Dirks et al. |
| 6,142,150 A | 11/2000 | O'Mahony |
| 6,148,814 A | 11/2000 | Clemmer et al. |
| 6,152,129 A * | 11/2000 | Berthon-Jones ......... 128/200.24 |
| 6,158,432 A | 12/2000 | Biondi et al. |
| 6,161,539 A | 12/2000 | Winter |
| 6,220,245 B1 | 4/2001 | Takabayashi et al. |
| 6,223,064 B1 | 4/2001 | Lynn et al. |
| 6,253,765 B1 | 7/2001 | Högnelid et al. |
| 6,257,234 B1 | 7/2001 | Sun |

(56) References Cited

U.S. PATENT DOCUMENTS

| | | |
|---|---|---|
| 6,269,812 B1 | 8/2001 | Wallace et al. |
| 6,273,444 B1 | 8/2001 | Power |
| 6,279,569 B1 | 8/2001 | Berthon-Jones |
| 6,283,119 B1 | 9/2001 | Bourdon |
| 6,286,508 B1 | 9/2001 | Remmers et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,342,039 B1 | 1/2002 | Lynn et al. |
| 6,357,438 B1 | 3/2002 | Hansen |
| 6,360,741 B2 | 3/2002 | Truschel |
| 6,360,745 B1 | 3/2002 | Wallace et al. |
| 6,369,838 B1 | 4/2002 | Wallace et al. |
| 6,371,114 B1 | 4/2002 | Schmidt et al. |
| 6,390,091 B1 | 5/2002 | Banner et al. |
| 6,412,483 B1 | 7/2002 | Jones et al. |
| 6,425,395 B1 | 7/2002 | Brewer et al. |
| 6,427,689 B1 | 8/2002 | Estes et al. |
| 6,439,229 B1 | 8/2002 | Du et al. |
| 6,467,478 B1 | 10/2002 | Merrick et al. |
| 6,484,719 B1 | 11/2002 | Berthon-Jones |
| 6,512,938 B2 | 1/2003 | Claure et al. |
| 6,532,957 B2 | 3/2003 | Berthon-Jones |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |
| 6,536,432 B2 | 3/2003 | Truschel |
| 6,539,940 B2 | 4/2003 | Zdrojkowski et al. |
| 6,543,449 B1 | 4/2003 | Woodring et al. |
| 6,546,930 B1 * | 4/2003 | Emerson et al. ......... 128/204.21 |
| 6,550,478 B2 | 4/2003 | Remmers et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,561,187 B2 | 5/2003 | Schmidt et al. |
| 6,571,795 B2 | 6/2003 | Bourdon |
| 6,575,163 B1 | 6/2003 | Berthon-Jones |
| 6,578,575 B1 | 6/2003 | Jonson |
| 6,609,016 B1 | 8/2003 | Lynn |
| 6,609,517 B1 | 8/2003 | Estes et al. |
| 6,615,834 B2 | 9/2003 | Gradon et al. |
| 6,622,726 B1 | 9/2003 | Du |
| 6,626,175 B2 | 9/2003 | Jafari et al. |
| 6,629,527 B1 | 10/2003 | Estes et al. |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,644,316 B2 * | 11/2003 | Bowman et al. ......... 128/207.12 |
| 6,659,101 B2 | 12/2003 | Berthon-Jones |
| 6,668,824 B1 | 12/2003 | Isaza et al. |
| 6,671,529 B2 | 12/2003 | Claure et al. |
| 6,675,801 B2 | 1/2004 | Wallace et al. |
| 6,688,307 B2 | 2/2004 | Berthon-Jones |
| 6,701,926 B2 | 3/2004 | Olsen et al. |
| 6,718,974 B1 | 4/2004 | Moberg |
| 6,722,365 B2 | 4/2004 | Nilsson et al. |
| 6,723,055 B2 | 4/2004 | Hoffman |
| 6,723,132 B2 | 4/2004 | Salehpoor |
| 6,725,447 B1 | 4/2004 | Gilman et al. |
| 6,739,337 B2 | 5/2004 | Isaza |
| 6,748,252 B2 | 6/2004 | Lynn et al. |
| 6,752,150 B1 | 6/2004 | Remmers et al. |
| 6,752,151 B2 | 6/2004 | Hill |
| 6,755,193 B2 | 6/2004 | Berthon-Jones et al. |
| 6,758,216 B1 | 7/2004 | Berthon-Jones et al. |
| 6,760,608 B2 | 7/2004 | Lynn |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,789,541 B2 | 9/2004 | Olsen et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,613 B2 | 11/2004 | Wenkebach et al. |
| 6,820,618 B2 | 11/2004 | Banner et al. |
| 6,823,866 B2 | 11/2004 | Jafari et al. |
| 6,837,242 B2 | 1/2005 | Younes |
| 6,843,250 B2 | 1/2005 | Efrati |
| 6,866,040 B1 | 3/2005 | Bourdon |
| 6,868,346 B2 | 3/2005 | Larson et al. |
| 6,874,503 B2 | 4/2005 | Rydgren |
| 6,910,480 B1 | 6/2005 | Berthon-Jones |
| 6,910,481 B2 | 6/2005 | Kimmel et al. |
| 6,920,875 B1 | 7/2005 | Hill et al. |
| 6,920,877 B2 | 7/2005 | Remmers et al. |
| 6,932,084 B2 | 8/2005 | Estes et al. |
| 6,945,248 B2 | 9/2005 | Berthon-Jones |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 7,000,612 B2 | 2/2006 | Jafari et al. |
| 7,008,380 B1 | 3/2006 | Rees et al. |
| 7,013,892 B2 | 3/2006 | Estes et al. |
| 7,017,576 B2 | 3/2006 | Olsen et al. |
| 7,036,504 B2 | 5/2006 | Wallace et al. |
| 7,040,320 B2 | 5/2006 | Fjeld et al. |
| 7,044,129 B1 | 5/2006 | Truschel et al. |
| 7,055,522 B2 | 6/2006 | Berthon-Jones |
| 7,066,173 B2 | 6/2006 | Banner et al. |
| 7,073,501 B2 | 7/2006 | Remmers et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,092,757 B2 | 8/2006 | Larson et al. |
| 7,100,607 B2 | 9/2006 | Zdrojkowski et al. |
| 7,100,608 B2 | 9/2006 | Brewer et al. |
| 7,100,609 B2 | 9/2006 | Berthon-Jones et al. |
| 7,107,991 B2 | 9/2006 | Kolobow |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,168,429 B2 | 1/2007 | Matthews et al. |
| 7,195,028 B2 | 3/2007 | Basset et al. |
| 7,210,478 B2 | 5/2007 | Banner et al. |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,331,343 B2 | 2/2008 | Schmidt et al. |
| 7,353,824 B1 | 4/2008 | Forsyth et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya et al. |
| 7,460,959 B2 | 12/2008 | Jafari |
| 7,475,685 B2 | 1/2009 | Dietz et al. |
| 7,487,773 B2 | 2/2009 | Li |
| 7,509,957 B2 | 3/2009 | Duquette et al. |
| 7,527,056 B2 | 5/2009 | Turiello |
| 7,533,671 B2 | 5/2009 | Gonzalez et al. |
| 7,621,269 B2 | 11/2009 | Turiello |
| 7,644,713 B2 | 1/2010 | Berthon-Jones |
| 7,654,802 B2 | 2/2010 | Crawford, Jr. et al. |
| 7,661,428 B2 | 2/2010 | Berthon-Jones |
| 7,673,629 B2 | 3/2010 | Turiello |
| 7,677,247 B2 | 3/2010 | Turiello |
| 7,694,677 B2 | 4/2010 | Tang |
| 7,694,678 B2 | 4/2010 | Turiello |
| 7,717,112 B2 | 5/2010 | Sun et al. |
| 7,717,113 B2 | 5/2010 | Andrieux |
| D618,356 S | 6/2010 | Ross |
| 7,770,578 B2 | 8/2010 | Estes et al. |
| 7,784,461 B2 | 8/2010 | Figueiredo et al. |

(56) References Cited

U.S. PATENT DOCUMENTS

| | | |
|---|---|---|
| 7,810,496 B2 | 10/2010 | Estes et al. |
| 7,810,497 B2 | 10/2010 | Pittman et al. |
| 7,814,906 B2 | 10/2010 | Moretti |
| 7,823,588 B2 | 11/2010 | Hansen |
| 7,827,988 B2 | 11/2010 | Matthews et al. |
| 7,855,716 B2 | 12/2010 | McCreary et al. |
| 7,856,979 B2 | 12/2010 | Doshi et al. |
| D632,796 S | 2/2011 | Ross et al. |
| D632,797 S | 2/2011 | Ross et al. |
| 7,882,835 B2 | 2/2011 | Eger et al. |
| 7,886,739 B2 | 2/2011 | Soliman et al. |
| 7,886,740 B2 | 2/2011 | Thomas et al. |
| 7,891,354 B2 | 2/2011 | Farbarik |
| 7,893,560 B2 | 2/2011 | Carter |
| 7,905,231 B2 | 3/2011 | Chalvignac |
| 7,918,222 B2 | 4/2011 | Chen |
| 7,918,223 B2 | 4/2011 | Soliman et al. |
| 7,920,067 B2 | 4/2011 | Durtschi et al. |
| 7,928,852 B2 | 4/2011 | Durtschi et al. |
| D638,852 S | 5/2011 | Skidmore et al. |
| 7,934,499 B2 | 5/2011 | Berthon-Jones |
| 7,938,114 B2 | 5/2011 | Matthews et al. |
| 7,963,283 B2 | 6/2011 | Sinderby |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,002,154 B2 | 8/2011 | Fontela et al. |
| D645,158 S | 9/2011 | Sanchez et al. |
| 8,021,309 B2 | 9/2011 | Zilberg |
| 8,021,310 B2 | 9/2011 | Sanborn et al. |
| 8,033,280 B2 | 10/2011 | Heinonen |
| D649,157 S | 11/2011 | Skidmore et al. |
| 8,051,853 B2 | 11/2011 | Berthon-Jones |
| 8,070,709 B2 | 12/2011 | Childers |
| 8,083,677 B2 | 12/2011 | Rohde |
| D652,521 S | 1/2012 | Ross et al. |
| D652,936 S | 1/2012 | Ross et al. |
| 8,105,310 B2 | 1/2012 | Klein |
| D653,749 S | 2/2012 | Winter et al. |
| 8,113,062 B2 | 2/2012 | Graboi et al. |
| 8,122,885 B2 | 2/2012 | Berthon-Jones et al. |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews et al. |
| 8,152,116 B2 | 4/2012 | Westberg |
| RE43,398 E | 5/2012 | Honkonen et al. |
| 8,181,643 B2 | 5/2012 | Friedberg |
| 8,181,648 B2 | 5/2012 | Perine et al. |
| 8,181,649 B2 | 5/2012 | Brunner |
| 8,187,184 B2 | 5/2012 | Muller et al. |
| 8,210,173 B2 | 7/2012 | Vandine |
| 8,210,174 B2 | 7/2012 | Farbarik |
| 8,211,128 B1 | 7/2012 | Facundus et al. |
| 8,216,159 B1 | 7/2012 | Leiboff |
| 8,217,218 B2 | 7/2012 | Court et al. |
| 8,225,796 B2 | 7/2012 | Davenport et al. |
| 8,235,930 B1 | 8/2012 | McCall |
| 8,240,684 B2 | 8/2012 | Ross et al. |
| 8,251,923 B2 | 8/2012 | Carrez et al. |
| 8,256,418 B2 | 9/2012 | Bassin |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,288,607 B2 | 10/2012 | Court et al. |
| 8,302,600 B2 | 11/2012 | Andrieux et al. |
| 8,302,602 B2 | 11/2012 | Andrieux et al. |
| 8,792,949 B2 | 7/2014 | Baker, Jr. |
| 2002/0014240 A1 | 2/2002 | Truschel |
| 2002/0053345 A1* | 5/2002 | Jafari et al. ............ 128/204.23 |
| 2002/0185126 A1 | 12/2002 | Krebs |
| 2003/0010339 A1 | 1/2003 | Banner et al. |
| 2003/0158466 A1 | 8/2003 | Lynn et al. |
| 2003/0159695 A1 | 8/2003 | Younes |
| 2003/0221689 A1 | 12/2003 | Berthon-Jones |
| 2004/0050387 A1 | 3/2004 | Younes |
| 2004/0074492 A1 | 4/2004 | Berthon-Jones |
| 2004/0089561 A1 | 5/2004 | Herman |
| 2004/0163648 A1 | 8/2004 | Burton |
| 2004/0187870 A1 | 9/2004 | Matthews et al. |
| 2005/0039748 A1 | 2/2005 | Andrieux |
| 2005/0109340 A1 | 5/2005 | Tehrani |
| 2005/0139212 A1 | 6/2005 | Bourdon |
| 2005/0172965 A1 | 8/2005 | Thulin |
| 2005/0188991 A1 | 9/2005 | Sun et al. |
| 2005/0241639 A1 | 11/2005 | Zilberg |
| 2006/0000475 A1 | 1/2006 | Matthews et al. |
| 2006/0011200 A1 | 1/2006 | Remmers et al. |
| 2006/0086357 A1 | 4/2006 | Soliman et al. |
| 2006/0102180 A1 | 5/2006 | Berthon-Jones |
| 2006/0112959 A1 | 6/2006 | Mechlenburg et al. |
| 2006/0118112 A1 | 6/2006 | Cattano et al. |
| 2006/0144144 A1 | 7/2006 | Seto |
| 2006/0150974 A1 | 7/2006 | Berthon-Jones |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0174883 A1 | 8/2006 | Aylsworth et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0217633 A1 | 9/2006 | Glocker et al. |
| 2006/0235324 A1 | 10/2006 | Lynn |
| 2006/0241708 A1 | 10/2006 | Boute |
| 2006/0247508 A1 | 11/2006 | Fennell |
| 2006/0249150 A1 | 11/2006 | Dietz et al. |
| 2006/0249156 A1 | 11/2006 | Moretti |
| 2006/0254588 A1 | 11/2006 | Brewer et al. |
| 2006/0264762 A1 | 11/2006 | Starr |
| 2006/0272642 A1 | 12/2006 | Chalvignac |
| 2006/0278218 A1 | 12/2006 | Hoffman |
| 2007/0000494 A1 | 1/2007 | Banner et al. |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044796 A1 | 3/2007 | Zdrojkowski et al. |
| 2007/0068530 A1 | 3/2007 | Pacey |
| 2007/0072541 A1 | 3/2007 | Daniels, II et al. |
| 2007/0077200 A1 | 4/2007 | Baker |
| 2007/0089738 A1 | 4/2007 | Soliman et al. |
| 2007/0093721 A1 | 4/2007 | Lynn et al. |
| 2007/0101992 A1 | 5/2007 | Soliman et al. |
| 2007/0129647 A1 | 6/2007 | Lynn |
| 2007/0135736 A1 | 6/2007 | Addington et al. |
| 2007/0144522 A1 | 6/2007 | Eger et al. |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0221224 A1 | 9/2007 | Pittman et al. |
| 2007/0227537 A1 | 10/2007 | Bemister et al. |
| 2007/0251532 A1 | 11/2007 | Friedberg |
| 2007/0272241 A1 | 11/2007 | Sanborn et al. |
| 2007/0277823 A1 | 12/2007 | Al-Ali et al. |
| 2007/0283958 A1 | 12/2007 | Naghavi |
| 2007/0284361 A1 | 12/2007 | Nadjafizadeh et al. |
| 2008/0000478 A1 | 1/2008 | Matthiessen et al. |
| 2008/0000479 A1 | 1/2008 | Elaz et al. |
| 2008/0041382 A1 | 2/2008 | Matthews et al. |
| 2008/0041383 A1 | 2/2008 | Matthews et al. |
| 2008/0051674 A1 | 2/2008 | Davenport et al. |
| 2008/0053441 A1 | 3/2008 | Gottlib et al. |
| 2008/0053442 A1 | 3/2008 | Estes et al. |
| 2008/0053443 A1 | 3/2008 | Estes et al. |
| 2008/0053444 A1 | 3/2008 | Estes et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |

(56) References Cited

U.S. PATENT DOCUMENTS

| | | |
|---|---|---|
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0168988 A1 | 7/2008 | Lu |
| 2008/0178880 A1 | 7/2008 | Christopher et al. |
| 2008/0178882 A1 | 7/2008 | Christopher et al. |
| 2008/0185002 A1 | 8/2008 | Berthon-Jones et al. |
| 2008/0200775 A1 | 8/2008 | Lynn |
| 2008/0200819 A1 | 8/2008 | Lynn et al. |
| 2008/0221469 A1 | 9/2008 | Shevchuk |
| 2008/0251079 A1 | 10/2008 | Richey |
| 2008/0295837 A1 | 12/2008 | McCormick et al. |
| 2008/0302359 A1 | 12/2008 | Loomas et al. |
| 2009/0014007 A1 | 1/2009 | Brambilla et al. |
| 2009/0050153 A1 * | 2/2009 | Brunner .............. 128/204.23 |
| 2009/0082653 A1 | 3/2009 | Rohde |
| 2009/0088613 A1 | 4/2009 | Marttila et al. |
| 2009/0093697 A1 | 4/2009 | Mir et al. |
| 2009/0137927 A1 | 5/2009 | Miller |
| 2009/0149730 A1 | 6/2009 | McCrary |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0178675 A1 | 7/2009 | Turiello |
| 2009/0178676 A1 | 7/2009 | Villax et al. |
| 2009/0194100 A1 | 8/2009 | Minagi |
| 2009/0205661 A1 | 8/2009 | Stephenson et al. |
| 2009/0205663 A1 | 8/2009 | Vandine et al. |
| 2009/0229605 A1 | 9/2009 | Efrati et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250061 A1 | 10/2009 | Marasigan |
| 2009/0272382 A1 | 11/2009 | Euliano et al. |
| 2009/0281481 A1 | 11/2009 | Harding |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0308398 A1 | 12/2009 | Ferdinand et al. |
| 2009/0314294 A1 | 12/2009 | Chalvignac |
| 2009/0318851 A1 | 12/2009 | Schenck |
| 2010/0011307 A1 | 1/2010 | Desfossez et al. |
| 2010/0018529 A1 | 1/2010 | Chalvignac |
| 2010/0024819 A1 | 2/2010 | Tiedje |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078018 A1 | 4/2010 | Heinonen |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0081958 A1 | 4/2010 | She |
| 2010/0101574 A1 | 4/2010 | Bassin |
| 2010/0101576 A1 | 4/2010 | Berthon-Jones |
| 2010/0116276 A1 | 5/2010 | Bayasi |
| 2010/0137737 A1 | 6/2010 | Addington et al. |
| 2010/0139660 A1 | 6/2010 | Adahan |
| 2010/0147303 A1 | 6/2010 | Jafari et al. |
| 2010/0186741 A1 | 7/2010 | Aylsworth et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0234758 A1 | 9/2010 | de Menezes |
| 2010/0236553 A1 | 9/2010 | Jafari et al. |
| 2010/0236555 A1 | 9/2010 | Jafari et al. |
| 2010/0242961 A1 | 9/2010 | Mougel et al. |
| 2010/0249549 A1 | 9/2010 | Baker, Jr. et al. |
| 2010/0252048 A1 | 10/2010 | Young et al. |
| 2010/0258123 A1 | 10/2010 | Somaiya et al. |
| 2010/0262038 A1 | 10/2010 | Tan et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2010/0331768 A1 | 12/2010 | Hedmann et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0034863 A1 | 2/2011 | Hoffa |
| 2011/0041849 A1 | 2/2011 | Chen et al. |
| 2011/0041850 A1 | 2/2011 | Vandine et al. |
| 2011/0061648 A1 | 3/2011 | Durtschi et al. |
| 2011/0071367 A1 | 3/2011 | Court et al. |
| 2011/0077549 A1 | 3/2011 | Kitai et al. |
| 2011/0100373 A1 | 5/2011 | Efrati et al. |
| 2011/0125052 A1 | 5/2011 | Davenport et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0178427 A1 | 7/2011 | Tan et al. |
| 2011/0196251 A1 | 8/2011 | Jourdain et al. |
| 2011/0201956 A1 | 8/2011 | Alferness et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0220112 A1 | 9/2011 | Connor |
| 2011/0226250 A1 | 9/2011 | LaBollita et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2011/0284003 A1 | 11/2011 | Douglas et al. |
| 2011/0290246 A1 | 12/2011 | Zachar |
| 2011/0293706 A1 | 12/2011 | Ludwig et al. |

(56) References Cited

U.S. PATENT DOCUMENTS

| | | |
|---|---|---|
| 2011/0313689 A1 | 12/2011 | Holley et al. |
| 2012/0000466 A1 | 1/2012 | Rapoport |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0006328 A1 | 1/2012 | Berthon-Jones |
| 2012/0022441 A1 | 1/2012 | Kelly et al. |
| 2012/0029317 A1 | 2/2012 | Doyle et al. |
| 2012/0030611 A1 | 2/2012 | Skidmore |
| 2012/0060835 A1 | 3/2012 | Mashak |
| 2012/0060841 A1 | 3/2012 | Crawford, Jr. et al. |
| 2012/0065533 A1 | 3/2012 | Carrillo, Jr. et al. |
| 2012/0071729 A1 | 3/2012 | Doyle et al. |
| 2012/0083729 A1 | 4/2012 | Childers |
| 2012/0090610 A1 | 4/2012 | O'Connor et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0139734 A1 | 6/2012 | Olde et al. |
| 2012/0150057 A1 | 6/2012 | Mantri |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0215081 A1 | 8/2012 | Euliano et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0255682 A1 | 10/2013 | Jafari et al. |
| 2013/0255685 A1 | 10/2013 | Jafari et al. |
| 2013/0284172 A1 | 10/2013 | Doyle et al. |
| 2013/0284177 A1 | 10/2013 | Li et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |

FOREIGN PATENT DOCUMENTS

| | | |
|---|---|---|
| EP | 1270036 | 1/2003 |
| EP | 1270036 A2 * | 1/2003 |
| WO | WO 94/23780 A | 10/1994 |
| WO | WO 98/06449 A | 2/1998 |
| WO | WO 00/10634 A | 3/2000 |
| WO | WO 00/45880 A | 8/2000 |
| WO | WO 01/74430 A | 10/2001 |
| WO | WO 02/28460 A | 4/2002 |
| WO | WO 03/055552 A1 | 7/2003 |
| WO | WO 2004000114 | 12/2003 |
| WO | WO 2004/084980 A | 10/2004 |
| WO | WO 2005/105189 | 11/2005 |
| WO | WO 2006/137784 A1 | 12/2006 |
| WO | WO 2007145948 | 12/2007 |
| WO | WO 2009123981 | 10/2009 |

OTHER PUBLICATIONS

Crooke, P.S. et al., "Patient-ventilator interaction: A general model for nonpassive mechanical ventilation", 1998, AMA Journal of Mathematics Applied in Medicine and Biology, 15, pp. 321-337.
U.S. Appl. No. 12/238,248, Office Action mailed Apr. 26, 2013, 13 pgs.
Jafari, M. et al., "Robust Feedback Design for Proportional Assist Ventilation-System Dynamics and Problem Definition" Decision and Control, 2005 and 2005 European Control Conference. CDC-E CC '05. 44TH IEEE Conference on Seville, Spain Dec. 12-15, 2005 (Dec. 12, 2005), pp. 4839-4844, XP010884460 DISBN: 978-0-7803-9567-1, the whole document.
PCT International Search Report and Written Opinion in Application PCT/2009/038810, mailed Jul. 6, 2009, 16 pgs.
PCT International Search Report and Written Opinion in Application PCT/2009/038815, mailed Jul. 1, 2009, 14 pgs.
PCT International Search Report and Written Opinion in Application PCT/US09/038811, mailed Jun. 7, 2009, 13 pgs.
PCT International Search Report and Written Opinion in Application PCT/US2009/038819, mailed Jun. 26, 2009, 12 pgs.
PCT International Search Report and Written Opinion in Application PCT/US2009/038820, mailed Jul. 22, 2009, 14 pgs.
PCT International Search Report and Written Opinion in Application PCT/US2009038818, mailed Jul. 14, 2009, 15 pgs.
PCT International Search Report and Written Opinion in Application PCT/US201/0026618, mailed Jun. 22, 2010, 19 pgs.
PCT International Search Report and Written Opinion in Application PCT/US2010/025485, mailed Feb. 27, 2009, 8 pgs.
U.S. Appl. No. 12/238,248, Office Action mailed Oct. 15, 2012, 12 pgs.
U.S. Appl. No. 12/238,248, Office Action mailed May 14, 2012, 12 pgs.
U.S. Appl. No. 12/242,741, Notice of Allowance mailed Jun. 5, 2012, 5 pgs.
U.S. Appl. No. 12/242,741, Office Action mailed Jan. 10, 2012, 7 pgs.
U.S. Appl. No. 12/242,741, Supplemental Notice of Allowability mailed Aug. 27, 2012, 2 pgs.
U.S. Appl. No. 12/242,756, Notice of Allowance mailed Jun. 5, 2012, 5 pgs.
U.S. Appl. No. 12/242,756, Office Action mailed Jan. 10, 2012, 7 pgs.
U.S. Appl. No. 12/242,756, Supplemental Notice of Allowability mailed Aug. 27, 2012, 2 pgs.
U.S. Appl. No. 12/334,354, Notice of Allowance mailed Jan. 27, 2012, 7 pgs.
U.S. Appl. No. 12/334,354, Notice of Allowance mailed Oct. 5, 2012, 5 pgs.
U.S. Appl. No. 12/395,332, Office Action mailed Sep. 13, 2012, 9 pgs.
U.S. Appl. No. 12/408,408, Notice of Allowance mailed Jun. 4, 2012, 10 pgs.
U.S. Appl. No. 12/408,414, Amendment and Response filed Sep. 5, 2012, 7 pgs.
U.S. Appl. No. 12/408,414, Office Action mailed Jun. 20, 2012, 9 pgs.
U.S. Appl. No. 12/414,419, Amendment and Response filed Aug. 27, 2012, 8 pgs.
U.S. Appl. No. 12/414,419, Notice of Allowance mailed Sep. 19, 2012, 8 pgs.
U.S. Appl. No. 12/414,419, Office Action mailed Jan. 20, 2012, 15 pgs.

(56) References Cited

OTHER PUBLICATIONS

U.S. Appl. No. 12/414,419, Office Action mailed Jul. 18, 2012, 16 pgs.
U.S. Appl. No. 13/565,595, Notice of Allowance mailed Nov. 2, 2012, 12 pgs.
U.S. Appl. No. 12/395,332, Notice of Allowance mailed Dec. 24, 2012, 8 pgs.
U.S. Appl. No. 12/408,414, Notice of Allowance mailed Dec. 10, 2012, 10 pgs.
U.S. Appl. No. 12/414,419, Notice of Allowance mailed Jan. 8, 2013, 7 pgs.
U.S. Appl. No. 12/238,248, Advisory Action mailed Jan. 4, 2013, 3 pgs.
U.S. Appl. No. 13/565,595, Notice of Allowance mailed Feb. 25, 2013, 8 pgs.

* cited by examiner

VENTILATOR LEAK COMPENSATION

RELATED PATENT APPLICATION

This application is a continuation application of U.S. patent application Ser. No. 12/414,419 (now U.S. Pat. No. 8,434,480), entitled "VENTILATOR LEAK COMPENSATION," filed on Mar. 30, 2009, which application claims priority from U.S. Provisional Application Ser. No. 61/041,070, which was filed on Mar. 31, 2008, the complete disclosures of which are hereby incorporated by reference in their entirety.

BACKGROUND

The present description pertains to ventilator devices used to provide breathing assistance. Modern ventilator technologies commonly employ positive pressure to assist patient ventilation. For example, after determining a patient-initiated or timed trigger, the ventilator delivers a specified gas mixture into an inhalation airway connected to the patient to track a specified desired pressure or flow trajectory, causing or assisting the patient's lungs to fill. Upon reaching the end of the inspiration, the added support is removed and the patient is allowed to passively exhale and the ventilator controls the gas flow through the system to maintain a designated airway pressure level (PEEP) during the exhalation phase. Other types of ventilators are non-triggered, and mandate a specified breathing pattern regardless of patient effort.

Modern ventilators typically include microprocessors or other controllers that employ various control schemes. These control schemes are used to command a pneumatic system (e.g., valves) that regulates the flow rates of breathing gases to and from the patient. Closed-loop control is often employed, using data from pressure/flow sensors.

Many therapeutic settings involve the potential for leaks occurring at various locations on the ventilator device. The magnitude of these leaks can vary from setting to setting, and/or dynamically within a particular setting, dependent upon a host of variables. Leaks can impair triggering (transition into inhalation phase) and cycling (transition into exhalation phase) of the ventilator; and thus cause problems with patient-device synchrony; undesirably increase patient breathing work; degrade advisory information available to treatment providers; and/or otherwise compromise the desired respiratory therapy.

Accordingly, attempts have been made in existing control systems to compensate for leaks in ventilator components. Though some benefits have been achieved, prior compensation mechanisms typically are predicated on simplified assumptions or limited information, which limits the ability to accurately and dynamically account for system leaks in general and instantaneous leak rates in particular.

DETAILED DESCRIPTION

Figure 1:
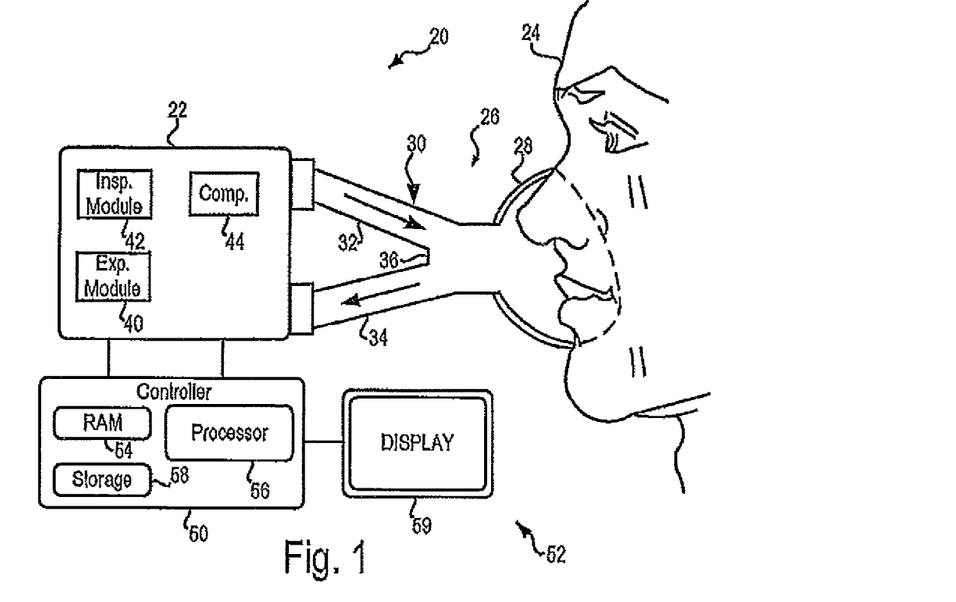
FIG. 1 is a schematic depiction of a ventilator.

FIG. 1 depicts a ventilator 20 according to the present description. As will be described in detail, the various ventilator system and method embodiments described herein may be provided with control schemes that provide improved leak estimation and/or compensation. These control schemes typically model leaks based upon factors that are not accounted for in prior ventilators, such as elastic properties and/or size variations of leak-susceptible components. The present discussion will focus on specific example embodiments, though it should be appreciated that the present systems and methods are applicable to a wide variety of ventilator devices.

Referring now specifically to FIG. 1, ventilator 20 includes a pneumatic system 22 for circulating breathing gases to and from patient 24 via airway 26, which couples the patient to the pneumatic system via physical patient interface 28 and breathing circuit 30. Breathing circuit 30 could be a two-limb or one-limb circuit for carrying gas to and from the patient. A wye fitting 36 may be provided as shown to couple the patient interface to the breathing circuit.

The present systems and methods have proved particularly advantageous in non-invasive settings, such as with facial breathing masks, as those settings typically are more susceptible to leaks. However, leaks do occur in a variety of settings, and the present description contemplates that the patient interface may be invasive or non-invasive, and of any configuration suitable for communicating a flow of breathing gas from the patient circuit to an airway of the patient. Examples of suitable patient interface devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. Compressor 44 is coupled with inspiratory module 42 to provide a gas source for ventilatory support via inspiratory limb 32.

The pneumatic system may include a variety of other components, including sources for pressurized air and/or oxygen, mixing modules, valves, sensors, tubing, accumulators, filters, etc. Controller 50 is operatively coupled with pneumatic system 22, signal measurement and acquisition systems, and an operator interface 52 may be provided to enable an operator to interact with the ventilator (e.g., change ventilator settings, select operational modes, view monitored parameters, etc.). Controller 50 may include memory 54, one or more processors 56, storage 58, and/or other components of the type commonly found in command and control computing devices. As described in more detail below, controller 50 issues commands to pneumatic system 22 in order to control the breathing assistance provided to the patient by the ventilator. The specific commands may be based on inputs received from patient 24, pneumatic system 22 and sensors, operator interface 52 and/or other components of the ventilator. In the depicted example, operator interface includes a display 59 that is touch-sensitive, enabling the display to serve both as an input and output device.

Figure 2:
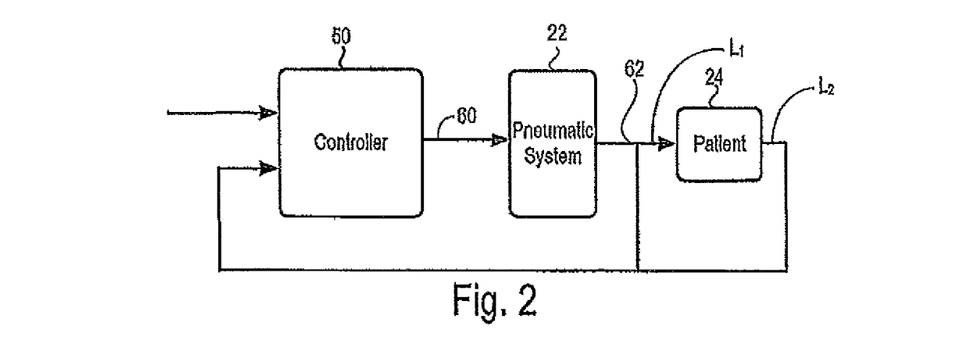
FIG. 2 schematically depicts control systems and methods that may be employed with the ventilator of FIG. 1.

FIG. 2 schematically depicts exemplary systems and methods of ventilator control. As shown, controller 50 issues control commands 60 to drive pneumatic system 22 and thereby circulate breathing gas to and from patient 24. The depicted schematic interaction between pneumatic system 22 and patient 24 may be viewed in terms of pressure and/or flow "signals." For example, signal 62 may be an increased pressure which is applied to the patient via inspiratory limb 32. Control commands 60 are based upon inputs received at controller 50 which may include, among other things, inputs from operator interface 52, and feedback from pneumatic system 22 (e.g., from pressure/flow sensors) and/or sensed from patient 24.

In many cases, it may be desirable to establish a baseline pressure and/or flow trajectory for a given respiratory therapy session. The volume of breathing gas delivered to the patient's lung and the volume of the gas exhaled by the patient are measured or determined, and the measured or predicted/estimated leaks are accounted for to ensure accurate delivery and data reporting and monitoring. Accordingly, the more accurate the leak estimation, the better the baseline calculation of delivered and exhaled volume as well as event detection (triggering and cycling phase transitions).

Figure 3A:
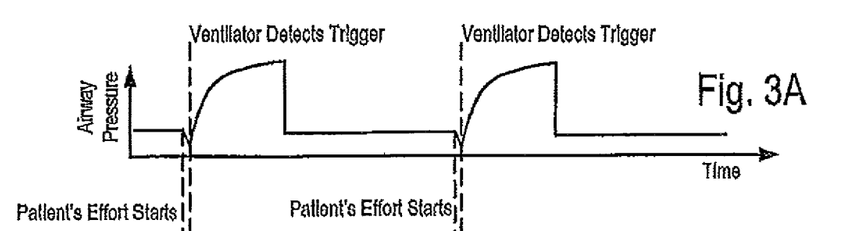
FIGS. 3A and 3B depict exemplary tidal breathing in a patient, and examples of pressure/flow waveforms observed in a ventilator under pressure support with and without leak condition. Under leak condition, the inhalation flow is the total delivered flow including the leak flow and the exhalation flow is the output flow rate measured by the ventilator and excludes the exhaled flow exhausted through the leak.
Figure 3B:
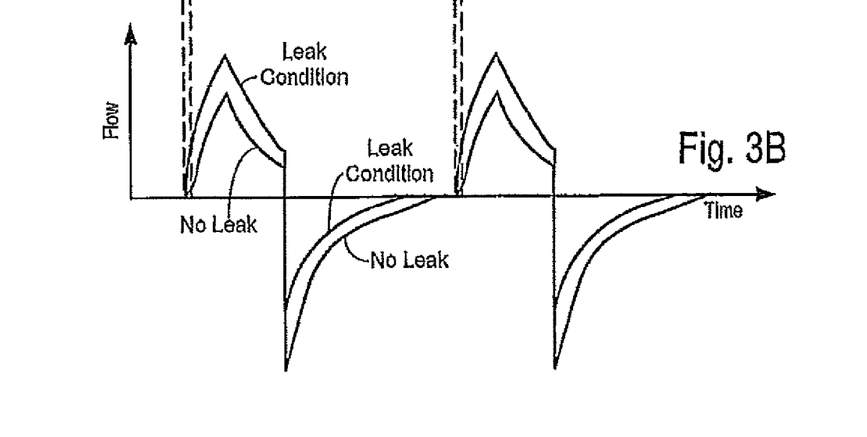

FIGS. 2, 3A and 3B may be used to illustrate and understand leak effects and errors. As discussed above, therapy goals may include generating a desired time-controlled pressure within the lungs of patient 24, and in patient-triggered and -cycled modes, achieve a high level of patient-device synchrony.

FIG. 3A shows several cycles of flow/pressure waveforms spontaneous breathing under Pressure Support mode with and without leak condition. As discussed above, a patient may have difficulty achieving normal tidal breathing, due to illness or other factors.

Regardless of the particular cause or nature of the underlying condition, ventilator 20 typically provides breathing assistance during inspiration and exhalation. FIG. 3B shows an example of flow waveform under Pressure Support in presence of no leak as well as leak conditions. During inspiration more flow is required (depending on the leak size and circuit pressure) to achieve the same pressure level compared to no leak condition. During exhalation, a portion of the volume exhaled by the patient would exit through the leak and be missed by the ventilator exhalation flow measurement subsystem. In many cases, the goal of the control system is to deliver a controlled pressure or flow profile or trajectory (e.g., pressure or flow as a function of time) during the inspiratory phase of the breathing cycle. In other words, control is performed to achieve a desired time-varying pressure or flow output 62 from pneumatic system 22, with an eye toward causing or aiding the desired tidal breathing shown in FIG. 3A.

Improper leak accounting can compromise the timing and magnitude of the control signals applied from controller 50 to pneumatic system 22 especially during volume delivery. Also, lack or inaccurate leak compensation can jeopardize spirometry and patient data monitoring and reporting calculations. As shown at schematic leak source $L_1$, the pressure applied from the pneumatic system 22 to patient interface 28 may cause leakage of breathing gas to atmosphere. This leakage to atmosphere may occur, for example, at some point on inspiratory limb 32 or expiratory limb 34, or at where breathing circuit 30 couples to patient interface 28 or pneumatic system 22.

Figure 4A:
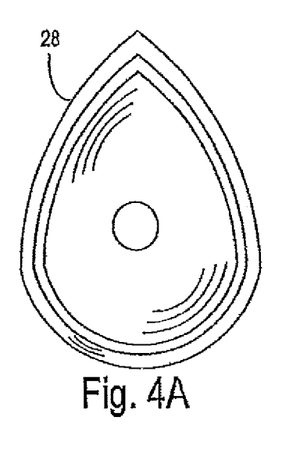
FIGS. 4A and 4B depict an example embodiment of the patient interface shown in FIG. 1.
Figure 4B:
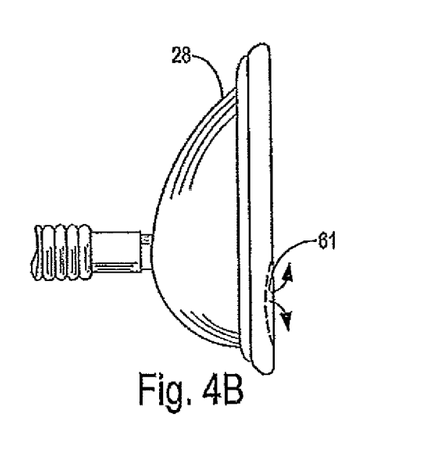

In the case of non-invasive ventilation, it is typical for some amount of breathing gas to escape via the opening defined between the patient interface (e.g., facial breathing mask) and the surface of the patient's face. In facial masks, this opening can occur at a variety of locations around the edge of the mask, and the size and deformability of the mask can create significant leak variations. As one example, as shown in FIG. 4A and FIG. 4B, the facial breathing mask may be formed of a deformable plastic material with elastic characteristics. Under varying pressures, during inspiration and expiration the mask may deform, altering the size of the leak orifice 61. Furthermore, the patient may shift (e.g., talk or otherwise move facial muscles), altering the size of leak orifice 61. Due to the elastic nature of the mask and the movement of the patient a leak compensation strategy assuming a constant size leak orifice may be inadequate.

Accurately accounting for the magnitude of leak $L_1$ may provide significant advantages. In order for controller 50 to command pneumatic system 22 to deliver the desired amount of volume/pressure to the patient at the desired time and measure/estimate the accurate amount of gas volume exhaled by the patient, the controller must have knowledge of how large leak $L_1$ is during operation of the ventilator. The fact that the leak magnitude changes dynamically during operation of the ventilator introduces additional complexity to the problem of leak modeling.

Triggering and cycling (patient-ventilator) synchrony may also be compromised by sub-optimal leak estimation. In devices with patient-triggered and patient-cycled modalities that support spontaneous breathing efforts by the patient, it can be important to accurately detect when the patient wishes to inhale and exhale. Detection commonly occurs by using accurate pressure and/or lung flow (flow rates into or out of the patient lung) variations. Leak source $L_2$ represents a leak in the airway that causes an error in the signals to the sensors of pneumatic system 22. This error may impede the ability of ventilator to detect the start of an inspiratory effort, which in turn compromises the ability of controller 50 to drive the pneumatic system in a fashion that is synchronous with the patient's spontaneous breathing cycles.

Improved leak estimation may be achieved in the present examples through provision of a control scheme that more fully accounts for factors affecting the time-varying magnitude of leaks under interface and airway pressure variations. The present example may include, in part, a constant-size leak model consisting of a single parameter (orifice resistance, leak conductance, or leak factor) utilized in conjunction with the pneumatic flow equation through a rigid orifice, namely, $$Q_{leak} = (\text{leak factor/Resistance/Conductance}) * \sqrt{\Delta P} \qquad (1)$$

Where ΔP=pressure differential across the leak site. This assumes a fixed size leak (i.e., a constant leak resistance or conductance or factor over at least one breath period).

To provide a more accurate estimate of instantaneous leak, the leak detection system and method may also take into account the elastic properties of one or more components of the ventilator device (e.g., the face mask, tubing used in the breathing circuit, etc.). This more accurate leak accounting enhances patient-ventilator synchrony and effectiveness under time-varying airway pressure conditions in the presence of both rigid orifice constant size leaks as well as pressure-dependent varying-size elastic leak sources.

According to the pneumatic equations governing the flow across an orifice, the flow rate is a function of the area and square root of the pressure difference across the orifice as well as gas properties. For derivation of the algorithm carried out by the controller, constant gas properties are assumed and a combination of leak sources comprising of rigid fixed-size orifices (total area=$A_r$=constant) and elastic opening through the patient interface [total area=$A_e(P)$ =function of applied pressure]. Therefore, $$Q_{leak}=K_o*(A_r+A_e(P))*\sqrt{\Delta P} \qquad (2)$$

$K_o$=assumed constant

For the purposes of this implementation, at low pressure differences, the maximum center deflection for elastic membranes and thin plates are a quasi-linear function of applied pressure as well as dependent on other factors such as radius, thickness, stress, Young's Modulus of Elasticity, Poisson's Ratio, etc. Therefore, $$A_e(P)=K_e*\Delta P \qquad (3)$$

$K_e$=assumed constant

As $\Delta P$ is the pressure difference across a leak source to ambient ($P_{ambient}$=0), then we substitute $\Delta P$ by the instantaneous applied pressure $P(t)$ and rearrange equation 1 as follows ($K_1$ and $K_2$ are assumed to be constant):

$$Q_{leak}=K_0(A_r+K_eP(t)\sqrt{P(t)} \qquad (4)$$

$$Q_{leak}=K_1*P(t)^{1/2}+K_2*P(t)^{3/2} \qquad (5)$$

Also, the total volume loss over one breath period=$V_{leak}$=Delivered Volume−Exhausted Volume;

$$V_{leak} = \int_0^{T_b}[K_1P(t)^{1/2}+K_2P(t)^{3/2}]dt \qquad (6)$$
$$= \int_0^{T_b}[Q_{delivered}-Q_{exh}]*dt$$

$T_b$ = full breath period

The general equation of motion for a patient ventilator system during passive exhalation can then be written, $$P_{aw}+P_m=R*(Q_{leak}+Q_{exh}-Q_{delivered})+(1/C)*\int[Q_{leak}+Q_{exh}-Q_{delivered}]*dt \qquad (7)$$

$P_{aw}$=airway pressure
$P_m$=muscle pressure
R=resistance
C=Compliance

Assuming that when end exhalation conditions are present a constant airway pressure is being delivered (steady PEEP), constant bias flow maintained during exhalation phase $Q_{delivered}$, constant leak flow (due to no pressure variation), and $P_m$=0 (due to no patient respiratory effort), the equation of motion could be differentiated and reorganized as follows:

$$\frac{dP_{aw}}{dt}=0=R*Q_{exh}dot+\frac{Q_{leak}+Q_{exh}-Q_{delivered}}{C} \qquad (8)$$

$$Q_{leak}=(Q_{delivered}-Q_{exh})-R*C*Q_{exh}dot \qquad (9)$$
$Q_{exh}dot$ = time derivative of exhausted flow If $Q_{exh}$dot=0 equation 8 can be reduced to $$Q_{leak}=Q_{delivered}-Q_{exh} \qquad (10)$$

And subsequently, $$Q_{leak}=K_1(PEEP)^{1/2}+K_2(PEEP)^{3/2} \qquad (11)$$

Otherwise $Q_{exh}$dot≠0. In this case, an appropriate duration of time $\Delta T$ is taken during passive exhalation period and assuming constant delivered flow, equation can be derived as follows:

$$R*C=\frac{(Q_{exh}(t+\Delta T)-Q_{exh}(t))}{(Q_{exh}dot(t+\Delta T)-Q_{exh}dot(t))} \qquad (12)$$

And, $$Q_{leak}(t_i+\Delta T)=K_1(PEEP)^{1/2}+K_2(PEEP)^{3/2}=[Q_{delivered}(t_i+\Delta T)-Q_{exh}(t_i+\Delta T)]-R*C*Q_{exh}dot(t_i+\Delta T) \qquad (13)$$

Therefore, equation 6 and equation 10 and equation 13 may be used to solve for $K_1$ and $K_2$. These calculations may be repeated every breath cycle and applied over appropriate time windows (i.e. during exhalation) and breathing conditions to optimize parameter estimation and minimize the total error between estimated total volume loss and actual measured volume loss across the full breath cycle. The constants $K_1$ and $K_2$ may be stored and compared to track changes and update various parameters of the system such as the triggering and cycling sensitivities, etc.

Figure 5:
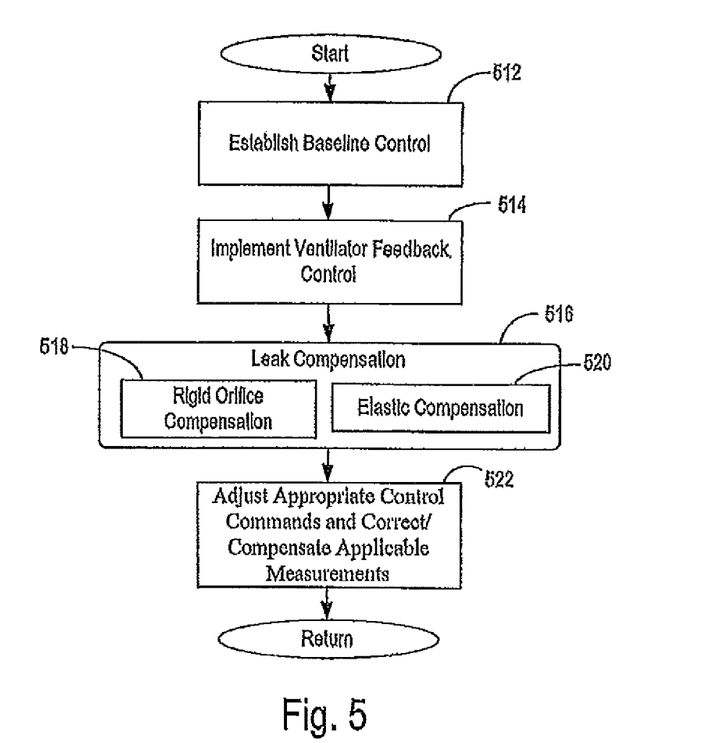
FIG. 5 depicts an exemplary method for controlling the ventilator of FIG. 1, including a method for compensating for leaks in ventilator components.

FIG. 5 shows an exemplary control strategy that may be implemented by the controller 50 to increase the accuracy and timing of the baseline breathing assistance provided by ventilator 20 and pneumatic system 22 for a variety of respiratory therapies. In this example, the method is repeated periodically every breathing cycle. In other examples, the dynamic updating of leak estimation may occur more or less than once per patient breathing cycle.

At 512 the routine establishes a baseline level of leak estimation and compensation. This may be a preset value stored in the controller 50 or may be updated taking into account various parameters of the breathing cycle and ventilator 20, such as the Positive End Expiratory Pressure PEEP, the set inspiratory pressure or flow/volume targets, the volumetric airflow delivered by pneumatic system 22, and type of the breathing circuit 30, etc.

The routine then proceeds to 514 where the feedback control (e.g., as shown in FIG. 3) is implemented. Various control regimes may be implemented, including pressure, volume and/or flow regulation. Control may also be predicated on inputs received from the patient, such as pressure variations in the breathing circuit which indicate commencement of inspiration. Inputs applied via operator interface 52 may also be used to vary the particular control regime used. For example, the ventilator may be configured to run in various different operator-selectable modes, each employing different control methodologies.

The routine advances to 516 where the leak compensation is performed. Various types of leak compensation may be implemented. For example, as shown at 518, rigid-orifice compensation may be employed using values calculated as discussed above. In particular, holes or other leak sources may be present in non-elastic parts of the breathing circuit, such as the ports of a facial mask (not shown) and/or in the inspiratory and expiratory limbs. Equation 1 may be used to calculate the volumetric airflow through such an orifice, assuming the leak factor/resistance/conductance is constant.

Elastic properties of ventilator components may also be accounted for during leak compensation, as shown at 520, for example using values calculated as described above. Specifically, elastic properties of patient interface 28 and/or breathing circuit 30 may be established (e.g., derived based on material properties such as elastic modulus, Poisson's ratio, etc.), and employed in connection with calculations such as those discussed above in reference to equations 6, 10, and/or 13, to account for the deformation of orifice 61, as shown in FIG. 4B. Using these example calculations, constants $K_1$ and $K_2$ may be solved for and updated dynamically to improve the accuracy of leak estimation. In alternate implementations, the method may use any suitable alternate mechanism or models for taking into account the elastic properties of a ventilator component having a leak-susceptible orifice.

The routine then proceeds to 522 where appropriate baseline control commands and measurements are adjusted to compensate for the leaks in the ventilator calculated in 616 i.e. adjust appropriate control command and correct and/or compensate applicable measurements. In many settings, it will be desirable to regularly and dynamically update the compensation level (e.g., once every breathing cycle) in order to optimize the control and compensation.

It will be appreciated that the embodiments and method implementations disclosed herein are exemplary in nature, and that these specific examples are not to be considered in a limiting sense, because numerous variations are possible. The subject matter of the present disclosure includes all novel and nonobvious combinations and subcombinations of the various configurations and method implementations, and other features, functions, and/or properties disclosed herein. Claims may be presented that particularly point out certain combinations and subcombinations regarded as novel and nonobvious. Such claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

What is claimed is:

1. A ventilator, comprising:
a pneumatic system for providing and receiving breathing gas;
a component for fluidly coupling the pneumatic system to a patient, wherein the component comprises a leak-susceptible orifice that varies in size during operation of the ventilator as a direct function of an applied pressure; and
a controller operatively coupled with the pneumatic system, wherein the controller is configured to:
control delivery of breathing gas to the patient, and
adjust at least one of a volume and pressure of breathing gas delivered to the patient to account for leakage from the pneumatic system, the adjustment based on the varying size of the leak-susceptible orifice.

2. The ventilator of claim 1, wherein the component is a patient interface.

3. The ventilator of claim 2, wherein the patient interface is a facial breathing mask.

4. The ventilator of claim 3, wherein the adjustment is based upon elastic and rigid leak properties of the facial breathing mask.

5. The ventilator of claim 1, wherein the adjustment is based upon an elastic modulus of a material comprising the component.

6. The ventilator of claim 1, further comprising an operator interface configured to accept operator input, the adjustment being dependent at least in part upon such operator input.

7. The ventilator of claim 6, wherein the controller is configured to establish elastic properties of the component based upon the operator input.

8. A ventilator, comprising:
a pneumatic system for circulating breathing gas to and from a patient;
an airway including a patient interface and a breathing circuit for fluidly coupling the pneumatic system with a patient, wherein the airway comprises a leak-susceptible orifice that varies in size as a direct function of an applied pressure; and
a controller operatively coupled with the pneumatic system, wherein the controller is configured to:
control delivery of breathing gas to the patient;
derive the varying size of the leak-susceptible orifice based on an elastic modulus of the airway and the applied pressure; and
adjust the delivery of breathing gas based on the varying size of the leak-susceptible orifice.

9. The ventilator of claim 8, wherein the controller is configured to dynamically update a magnitude of the adjustment during operation of the ventilator.

10. The ventilator of claim 9, where the controller is configured to dynamically update the magnitude of the adjustment during each of a plurality of breathing cycles.

11. The ventilator of claim 8, where the patient interface comprises a facial breathing mask which at least partly defines the leak-susceptible orifice.

12. In a ventilator having a pneumatic system and an airway adapted to fluidly couple the pneumatic system to a patient, a leak compensation method, comprising:
providing a baseline level of leak compensation based upon a size of a leak-susceptible orifice in the airway;
deriving elastic properties of a component of the airway containing the leak-susceptible orifice based at least in part on material properties of the component;
adjusting the baseline level of leak compensation in response to a pressure sufficient to cause deformation of the leak-susceptible orifice, wherein an extent of the deformation of the leak-susceptible orifice is based upon the elastic properties of the component and is a direct function of the pressure, and wherein a magnitude of the adjustment is based on the elastic properties of the component.

13. The method of claim 12, wherein the component is a patient interface.

14. The method of claim 13, wherein the patient interface is a facial ventilator mask.

15. The method of claim 12, wherein the component is a breathing circuit fluidly coupled between the patient and the pneumatic system.

16. The method of claim 12, wherein adjusting the baseline level of leak compensation is performed during a plurality of patient breathing cycles.

17. The method of claim 16, wherein the magnitude of the adjustment is dynamically updated at least once per breathing cycle.

18. The method of claim 12, further comprising accepting operator input at an operator interface of the ventilator, and using the operator input in the deriving of the elastic properties of the component.

19. A ventilator, comprising:

a pneumatic system for providing and receiving breathing gas;

an airway including a patient interface and a breathing circuit for fluidly coupling the pneumatic system with a patient; and a controller operatively coupled with the pneumatic system, where the controller is configured to:

control a flow of breathing gas to the patient, and make dynamic adjustments in the flow of the breathing gas to compensate for a leak in the airway, where the dynamic adjustments are based at least in part on rigid leak properties of a fixed-size orifice of the airway and elastic leak properties of a variable-size orifice of the airway, and where the elastic leak properties of the variable-size orifice of the airway are a direct function of an applied pressure.

20. The ventilator of claim 19, where the patient interface is a facial ventilator mask.

* * * * *